United States Patent [19]

Rohr et al.

[11] 4,412,904

[45] Nov. 1, 1983

[54] ELECTROCHEMICAL MEASURING CELL

[75] Inventors: Franz-Josef Rohr, Abtsteinach; Andreas Reich, Heidelberg, both of Fed. Rep. of Germany

[73] Assignee: Brown, Boveri & Cie AG, Mannheim-Käfertal, Fed. Rep. of Germany

[21] Appl. No.: 398,549

[22] Filed: Jul. 15, 1982

[30] Foreign Application Priority Data

Jul. 21, 1981 [DE] Fed. Rep. of Germany ....... 3128738

[51] Int. Cl.³ ............................................ G01N 27/26
[52] U.S. Cl. .................................................. 204/424
[58] Field of Search ..................................... 204/195 S

[56] References Cited

U.S. PATENT DOCUMENTS

| 4,040,930 | 8/1977 | Dillon | 204/195 S |
|---|---|---|---|
| 4,127,464 | 11/1978 | Ichikawa et al. | 204/195 S |
| 4,225,634 | 9/1980 | Tanaka et al. | 204/195 S |
| 4,233,142 | 11/1980 | Rohr et al. | 204/195 S |
| 4,278,509 | 7/1981 | Otsuka et al. | 204/195 S |
| 4,283,441 | 8/1981 | Haecker et al. | 204/195 S |
| 4,304,651 | 12/1981 | Wakizaka | 204/195 S |
| 4,304,652 | 12/1981 | Chiba et al. | 204/195 S |
| 4,339,320 | 10/1980 | Friese et al. | 204/195 S |

Primary Examiner—Arthur P. Demers
Attorney, Agent, or Firm—Herbert L. Lerner; Laurence A. Greenberg

[57] ABSTRACT

An electrochemical measuring cell, in particular for the determination of the oxygen content in gases, which has an ion-conducting, solid electrolyte. The latter is provided with at least one electrode in the form of a porous layer containing electron-conducting, ceramic oxide material.

For the improvement of the electron-conductivity of the electrode there is embedded in the layer metallic material such as a metal wire whose electron-conductivity is greater than the electron-conductivity of the oxide material. Only as much metallic material need be added to increase the electron-conductivity of the electrode sufficiently to a predetermined value.

7 Claims, 10 Drawing Figures

ELECTROCHEMICAL MEASURING CELL

BACKGROUND OF THE INVENTION

1. Field of the Invention

The invention relates to an electrochemical measuring cell, in particular for the determination of the oxygen content in gases, with a solid electrolyte having at least one electrode designed in the form of at least one porous layer containing electron-conducting, ceramic oxide material.

2. Description of the Prior Art

Due to its electrodes containing ceramic oxide material, an electrochemical measuring cell of this kind, disclosed in German Pat. No. 2,738,755, has great thermal and chemical stability as well as good catalytic effectiveness, but the electron-conductivity and, hence, the current-carrying capacity of the electrodes leaves something to be desired.

SUMMARY OF THE INVENTION

Therefore, it is an object of the invention to provide an analyzer of the kind described at the outset, in which the electron-conductivity of the electrodes is improved while retaining a high percentage of ceramic oxide material. The analyzer can be manufactured at low cost and meets the requirements occurring in operation.

With the foregoing and other objects in view, there is provided in accordance with the invention an electrochemical measuring cell, in particular for the determination of the oxygen content in gases, having a solid electrolyte and at least one electrode connected to the electrolyte for the transfer of an electric current by the flow of electrons therebetween, the improvement comprising disposing the electrode on the electrolyte in the form of a layer containing electron-conducting ceramic material together with a metallic material having an electron-conductivity greater than the electron-conductivity of the ceramic material in an amount sufficient to increase the electron-conductivity of the electrode to a predetermined value. Other features which are considered as characteristic for the invention are set forth in the appended claims.

Although the invention is illustrated and described herein as embodied in the electrochemical measuring cell, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings in which.

DETAILED DESCRIPTION OF THE INVENTION

Figure 1:
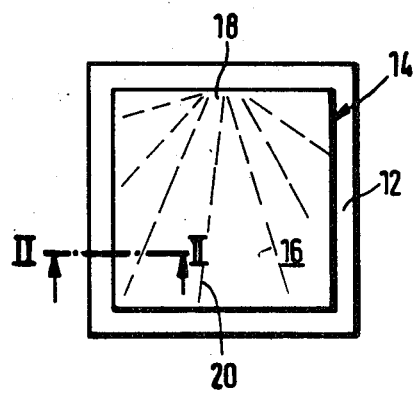
FIG. 1 diagrammatically illustrates a rectangular, solid electrolyte with a plane surface of an electrode applied to the plane surface of the electrolyte in a thin layer, and metal wires fanning out from a contact embedded in the layer.

According to the invention, the metallic material whose electron-conductivity is greater than the electron-conductivity of the oxide material is contained in the layer in an amount at least sufficient to increase the electron-conductivity of the electrode to a predetermined electron-conductivity.

Accordingly, metallic material of high electron-conductivity is embedded in the layer forming the electrode, hence increasing the electron-conductivity of the electrode overall to increase it, preferably by a factor of at least 5, desirably by a factor of at least 10. The metallic material may be any conventionally used metal capable of withstanding the thermal and chemical stresses occurring during the operation of the analyzer. The term "metals" in the present invention is understood to include, in addition to technically pure metals, metal alloys and, if applicable, heterogeneous mixtures of metals or metal alloys.

One will use as metallic material, especially for catalytically effective elctrodes, noble metals such as gold, silver and the so called platinum metals comprising platinum, ruthenium, rhodium, palladium, osmium and iridium. In many cases it may suffice, however, to use temperature-resistant nickel- and chromium-containing alloys.

An advantageous further development of the invention resides in that the metallic material share need fill at most fifty percent, and preferably no more than thirty percent of the volume of the electrode. In particular, the percentage is 2 to 20%. The smaller values of the above ranges will be used for the most part when metallic material in the form of wires or strip conductors is employed. In one embodiment according to FIG. 8, the percentage will be closer to the upper limit. With a low volume percent metal, sufficient electron-conductivity of the electrode is coupled with a low cost for the metallic material. This is important especially when noble metals are used.

A simple design results when the metallic material advantageously consists of at least one metal wire embedded in the layer.

Another advantageous embodiment resides in having the metallic material in the form of at least one conductor strip applied to the solid electrolyte and covered by the ceramic layer. Such conductor strips are known in electrical engineering in printed electrical circuits. In many such cases, e.g. when long, strip-shaped electrodes of small width or long, ring-cylindrical electrodes are involved, a single metal wire or conductor strip running length-wise may be sufficient.

It is recommended for the further improvement of the electron-conductivity of the electrode that the metal wire or conductor strip extend from the area of the electrical terminal of the electrode to the connectionless area. The metal wire or conductor strip may be brought directly to the site of the electrical terminal and, if applicable, the wire or strip make direct contact with the electrical lead there.

In an especially preferred further development of the invention, the metallic material consists of small particles embedded, preferably uniformly, in the layer. The shape of the particles may be arbitrary, its largest dimension preferably amounting to no more than fifty percent of the layer thickness. These particles may also consist of catalytically active material.

It is simplest in many cases if the particles consists of solid metallic material.

Another advisable further development which combines good electron-conductivity of the layer with low material consumption, is characterized by the particles having a core of preferably electron-conducting ceramic material and a jacket of metallic material. Due to this additional core construction of electron-conducting ceramic material, the jacket can be very thin in relation to the size of the particles, and yet adequate electron-conductivity of the particles can be obtained.

If the electrode is to have catalytic effectiveness, the jacekt, at least, will contain a catalytically active metallic material. Such material is preferably a material or an alloy of the platinum group. In addition, making the core of catalytically active oxide material is also recommended.

Further advantages and features of the invention will be evident from the following description of embodiment examples in connection with the schematic drawings.

In the various figures, identical parts have the same reference symbols.

FIG. 1 is a view of a solid electrolyte 12 having a rectangular contour contained in one place of an electrochemical measuring cell according to the invention. Applied to the top surface of the solid electrolyte 12 is an electrode 14 in the form of a thin layer 16. This layer 16 also has a plane surface and is spaced from the outer contour of the solid electrolyte 12 at a distance which is small in relation to the side length of the electrolyte 12. At the upper edge of the layer 16, in the middle, is the contact 18 where the measuring signal is taken off the electrode, e.g. through a pressed-on electrical contact.

From this contact 18, straight metal wires 20 start and traverse uniformly and in sunburst fashion through the layer 16 to the areas remote from the contact 18. In FIG. 1, these metal wires are represented by broken lines.

Figure 2:
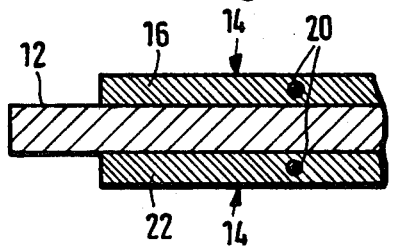
FIG. 2 is an enlarged section along line II—II of FIG. 1 and shows a thin layer electrode on each side of the electrolyte with wires embedded in the electrodes.

FIG. 2, showing the cross section II—II of FIG. 1 on a larger scale, clearly illustrates the arrangement of a metal wire 20 in the layer 16. If another layer 22 is provided on the solid electrolyte opposite the layer 16, metal wires 20 may also be embedded in it, in a manner corresponding to layer 16.

Figure 3:
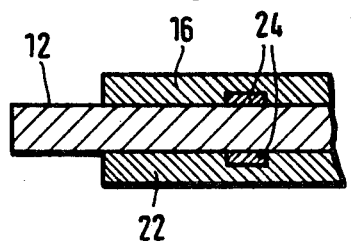
FIG. 3 is a variant of FIG. 2 in that the metal in layers are conductor strips.

FIG. 3 shows an embodiment variant corresponding to FIG. 2. Here, a conductor strip 24 is disposed in each of the layers 16 and 22. Such conductor strips are known in electrical engineering in connection with printed circuits. Of course, deviating from FIG. 1, the metal wires 20 or conductor strips 24 may also wind or meander through their respective layers. In some cases it may also be advisable to provide wire screens or conductors designed in net form to penetrate a large area of the electrodes.

Figure 4:
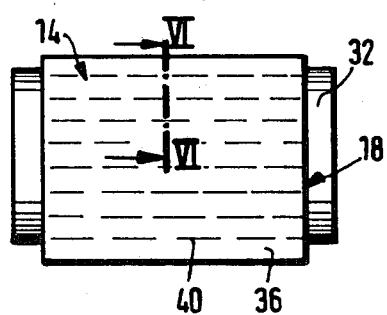
FIG. 4 is a side view of a tubular or ring-cylindrical, solid electrolyte and a layer electrode in which axially extending metal wires are embedded.
Figure 6:
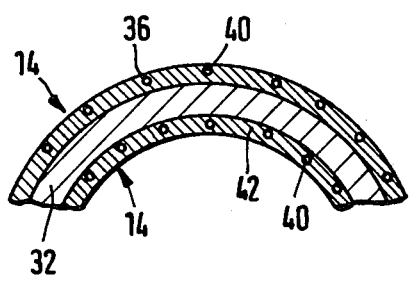
FIG. 6 is an enlarged transverse section of FIG. 4 taken along line VI—VI of FIG. 4.

Shown in FIG. 4 is a side view of a ring-cylindrical solid electrolyte 32 of an electrochemical measuring cell according to the invention. The inner and outer cylinder surfaces of the solid electrolyte 32 in the form of a cylindrical wall are respectively provided with an outer layer 36 and inner layer 42, each layer forming the electrode, as may be seen clearly in the cross section according to FIG. 6. Embedded in each electrode 36 and 42 are straight metal wires 40, extending axially over the entire length of the electrodes. The contact 18 is here in the form of an annular area, at least at one axial end of the electrode.

Figure 7:
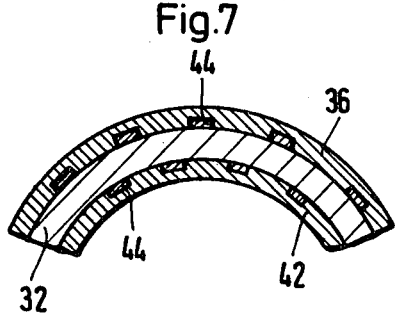
FIG. 7 is a variant of FIG. 6.

Here again, electrical contactor strips 44 as shown in FIG. 7 may be embedded in the layers 36, 42 instead of the metal wires 40. The metal wires or conductor strips may also be joined to form nets.

Figure 5:
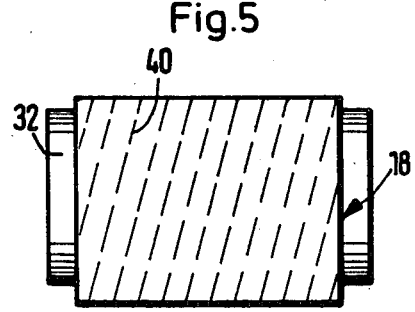
FIG. 5 is a variant of FIG. 4 with a helically wound metal wire extending axially in the layer.

An embodiment variant, especially for ring-cylindrical measuring cells, is a helically wound arrangement of the metal wires or conductor strips, as shown in a side view in FIG. 5.

Although electrochemical measuring cells with open ends are shown in FIGS. 4 and 5, the invention is naturally also applicable to measuring cells with one end closed by being capped and covered by electrodes. In such instance, the metal wires or conductor strips would, if applicable, also extend over the caps.

Figure 8:
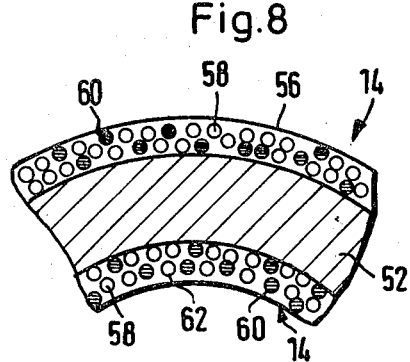
FIG. 8 is a sector of a ring-cylindrical electrolyte and electrodes of the measuring cell in transverse section.

FIG. 8 shows, greatly enlarged, a sector of a ring-cylindrical measuring cell in cross section as an embodiment variant. On the solid electrolyte 52 is an outer layer 56 and, optionally, an inner layer 62, forming the electrodes 14. Here, the layers 56, 62 consist of oxide material in the form of granules 58, of which only the contour is shown. Embedded between these granules 58 and uniformly distributed are small metallic particles 60, likewise in granular form. The particles 60 are represented as black dots.

The particles 60 may consist of solid, metallic material or, to save metallic material, they may each have a core 64 of ceramic oxide material surrounded by a metallic jacket 68. In relation to the size of a particle 60, the wall thickness of a jacket 68 is very thin, as may be clearly seen in FIG. 9.

Figure 9:
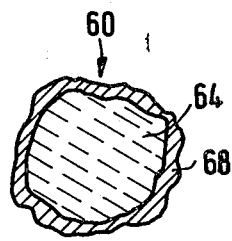
FIG. 9 diagrammatically illustrates a particle, greatly enlarged, for the construction of a layer.
Figure 10:
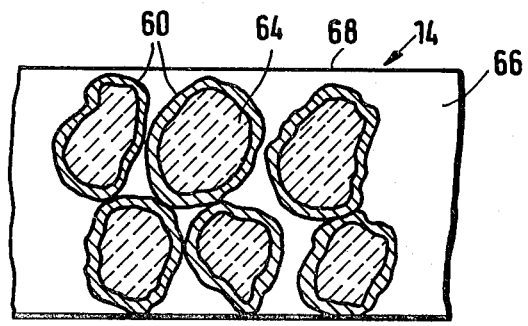
FIG. 10 shows the construction of a layer of particles according to FIG. 9.

Finally, FIG. 10 shows, greatly enlarged, a cross section of a layer 66. This is a modification of the layers according to FIG. 8, in that particles 60 only are provided here, each particle 60 having a core 64 of ceramic oxide material and a jacket 68 of metallic material. Therefore, the particles 60 correspond to those of FIG. 9, and the explanations pertaining to that FIG. 9 also apply here. The construction of a layer according to FIG. 10 provides high electron-conductivity of the electrode at low metallic material cost. The electron-conductivity of the electrodes can be further improved by producing the core 64 of electron-conducting, ceramic material. Also, catalytic effectiveness can be imparted to the layer by appropriately selecting the material for the jackets 68.

The following guide values or production guidelines may be used for the construction of measuring cells according to the invention. In the embodiment examples according to FIGS. 1 to 8, the thickness of the solid electrolyte is approximately 0.5 to 2 mm, and the thickness of the layers forming the electrodes approximately 0.05 to 0.3 mm. The wires or conductor strips disposed in the layers are approximately 0.03 to 0.1 mm thick, with a conductor strip width of 1 to 4 mm. The layers for the measuring cells according to FIGS. 1 to 7 are produced by plasma-spraying the ceramic oxide powder on the solid electrolyte surface on which the metal wires or metal nets have been laid or wound, or by applying a ceramic oxide powder suspension with subsequent drying and sintering. If a conductor strip is used, it must be applied by vapor depositing, sputtering or chemical vapor deposition (CVD) prior to the application of the layer. It is also possible to apply a metal suspension in strips, to be subsequently solidified by drying and firing.

In the above-described measuring cells, the metal wire or the electrical conductor strips should have a thermal expansion behavior at least approximately equal to that of the associated layer. However, when metal wires are used which are relatively thin in proportion to the thickness of the associated layer, differences in the thermal expansion behavior are by far less critical than with relatively thick wires. Also, differences in the expansion behavior with great layer porosity and/or with helically wound metal wires are less critical. This applies logically to conductor strips also.

The thickness of the layers in the embodiment examples according to FIGS. 8 and 10 is approximately 0.05 to 0.3 mm; the maximum thickness or the maximum diameter of the particles is approximately 0.01 to 0.08 mm, and the same applies to the ceramic oxide material granules 58. To produce the layer, ceramic oxide powder is stirred until a metal suspension or metal plate is obtained and the paste then is applied to the solid electrolyte surface. After drying, the layer is fired-on at a temperature of 900° to 1100° C. But it is also possible to mix the powdery oxide material and the fine-grained metallic material, to add a liquid organic dispersing agent such as amylacetate nitrocellulose, and to apply it according to the above.

The size or diameter of a particle according to FIG. 9 is 0.1 mm max, the size range mostly used being 0.02 to 0.08 mm. The thickness of the metallic jacket 68 is approximately 1/5 to 1/25 of the particle size. To produce the particles according to FIG. 9, granules of appropriate size of a ceramic oxide powder are impregnated with a metal salt solution or a solution of an organo-metallic compound of the metal, and the metallic jacket is produced by subsequent thermal decomposition of the salt or of the organo-metallic compound.

The guide values given for FIG. 8 apply roughly also to the embodiment example according to FIG. 10.

The electron-conducting ceramic material used to produce the layers may consists, for example, of a material of the composition La Me $O_3$, doped with strontium, calcium, barium or aluminum, Me meaning cobalt, nickel, manganese or chromium. The composition of other layers of this kind is described in German Pat. No. 2,738,755. For oxygen measurements, the solid electrolyte contains oxygen ion-conducting material, e.g. zirconium oxide stabilized with calcium oxide.

The current-carrying capacity of the electrodes of a measuring cell according to the invention is approximately 3 to 5 times as high as that of measuring cell with electrodes containing ceramic oxide material only.

The electrochemical oxygen exchange relative to one square centimeter of electrode is also increased by about a factor 3 to 5 in the measuring cells according to the invention over measuring cells with conventional, oxidic electrodes; even over analyzers with noble metal electrodes such as of platinum, the analyzer according to the invention shows an improvement by about a factor 2. The term "electrochemical oxygen exchange" means the process occurring on and in the electrodes during operation, especially the transport, greatly influenced by the porosity of the electrode, of the reactants to and from the electrode. The above term also includes the charge exchange and the catalytic effectiveness.

The spacing of the wires, conductor strips or, if applicable, the mesh size of the screens in the embodiment examples according to FIGS. 1 to 7 should amount to no more than 200 times, preferably no more than 50 times the wire diameter or conductor strip thickness.

Electrodes designed in accordance with the present invention are preferably used in those measuring cells from which an electric current is derived during operation, or to which such a current is conducted. This electric current is a measure of the gas component to be determined.

There are claimed:

1. In an electrochemical measuring cell, in particular for the determination of the oxygen content in gases, having a solid electrolyte and at least one electrode connected to the electrolyte for the transfer of an electric current by the flow of electrons therebetween, the improvement comprising disposing the electrode on the electrolyte in the form of a layer containing electron-conducting ceramic material together with a metallic material having an electron-conductivity greater than the electron-conductivity of the ceramic material in an amount sufficient to increase the electron-conductivity of the electrode to a predetermined value, said metallic material consisting of small solid particles containing only metallic material, and said small particles embedded in the layer without substantial loss of particulate identity.

2. In an electrochemical measuring cell, in particular for the determination of the oxygen content in gases, having a solid electrolyte and at least one electrode connected to the electrolyte for the transfer of an electric current by the flow of electrons therebetween, the improvement comprising disposing the electrode on the electrolyte in the form of a layer containing electron-conducting ceramic material together with a metallic material having an electron-conductivity greater than the electron-conductivity of the ceramic material in an amount sufficient to increase the electron-conductivity of the electrode to a predetermined value, said metallic material consisting of small solid particles containing a core of electron conducting ceramic material and a jacket of a catalytically active metallic material, and said small particles embedded in the layer without substantial loss of particulate identity.

3. Electrochemical measuring cell according to claim 1 or 2, wherein the metallic particles occupy approximately 2-20% of the volume of the electrode.

4. Electrochemical measuring cell according to claim 1 or 2, wherein the metallic particles occupy no more than 30% of the volume of the electrode.

5. Electrochemical measuring cell according to claim 1 or 2, wherein the metallic particles occupy no more than 50% of the volume of the electrode.

6. Electrochemical measuring cell according to claim 1 or 2, wherein the metallic particles are arranged in the layer to effect at least an approximately uniform distribution.

7. Electrochemical measuring cell according to claim 1 or 2, wherein the metallic particles have a thermal expansion behavior approximately equal that of the associated layer.

* * * * *